United States Patent
Galvan Gonzalez

(10) Patent No.: US 8,865,136 B2
(45) Date of Patent: Oct. 21, 2014

(54) ANTISEPTIC PHARMACEUTICAL COMPOSITION FOR ORAL HYGIENE AND THE TREATMENT OF ORAL DISEASES OF MICROBIAL ORIGIN

(76) Inventor: Tomas Bernardo Galvan Gonzalez, Santiago (CL)

( * ) Notice: Subject to any disclaimer, the term of this patent is extended or adjusted under 35 U.S.C. 154(b) by 0 days.

(21) Appl. No.: 13/391,334

(22) PCT Filed: Aug. 19, 2010

(86) PCT No.: PCT/CL2010/000030
§ 371 (c)(1),
(2), (4) Date: Feb. 20, 2012

(87) PCT Pub. No.: WO2011/020206
PCT Pub. Date: Feb. 24, 2011

(65) Prior Publication Data
US 2012/0148506 A1    Jun. 14, 2012

(30) Foreign Application Priority Data

Aug. 20, 2009   (CL) .................................. 1747-2009

(51) Int. Cl.
A61K 33/40   (2006.01)
A61P 1/02    (2006.01)
A61P 31/00   (2006.01)
A61K 8/27    (2006.01)
A61K 8/49    (2006.01)
A61K 8/22    (2006.01)
A61K 8/34    (2006.01)
A61Q 11/00   (2006.01)
A61K 8/21    (2006.01)
A61K 8/35    (2006.01)

(52) U.S. Cl.
CPC . *A61Q 11/00* (2013.01); *A61K 8/27* (2013.01); *A61K 8/4926* (2013.01); *A61K 8/22* (2013.01); *A61K 8/347* (2013.01); *A61K 8/21* (2013.01); *A61K 8/345* (2013.01); *A61K 8/35* (2013.01)
USPC ............................... 424/49; 424/52; 424/613

(58) Field of Classification Search
USPC ...................................................... 424/49, 53
See application file for complete search history.

(56) References Cited

U.S. PATENT DOCUMENTS

| | | | | |
|---|---|---|---|---|
| 4,436,721 A | * | 3/1984 | Gaffar | 424/52 |
| 2008/0247972 A1 | * | 10/2008 | Conceicao | 424/52 |
| 2009/0081134 A1 | * | 3/2009 | Pan et al. | 424/49 |

FOREIGN PATENT DOCUMENTS

WO        WO00/00166        * 1/2000

* cited by examiner

*Primary Examiner* — Walter Webb
(74) *Attorney, Agent, or Firm* — Hasse & Nesbitt LLC; Daniel F. Nesbitt

(57) ABSTRACT

A polyantiseptic antimicrobial pharmaceutical composition for oral use, for the hygiene and treatment of oral diseases of bacterial, mycotic or viral etiology, for over-the-counter sale, without contraindications. The composition does not contain phenolic or, chlorophenolic compounds, and consists of a mixture of hydrogen peroxide, eugenol, natural camphor, zinc sulphate, sodium fluoride, xylitol, cetylpyridinium chloride and excipients. The formulation is used to deodorise, disinfect, astringe and soothe inflammation of the oral area, avoids the neoformation of bacterial plaque, prevents tooth cavities, inhibits the formation of dental tartar, improves the resistance of teeth to cavities, and treats and prevents oral aphthous ulcers.

12 Claims, No Drawings

ANTISEPTIC PHARMACEUTICAL COMPOSITION FOR ORAL HYGIENE AND THE TREATMENT OF ORAL DISEASES OF MICROBIAL ORIGIN

FIELD OF THE INVENTION

The present invention consists of a pharmaceutical composition for oral use, of antiseptic action, of broad spectrum in the form of a mouth wash or other forms of presentation, which are useful to prevent or cure oral illnesses originated by germs.

The vast majority of oral diseases are caused by microorganisms present in the mouth. The most prevalent ones are tooth decay, gum disease, and halitosis, and to a lesser extent, mucositis, candidiasis, aphta among other. These infectious diseases may comprise the oral health of 80% or more of the world's population and recent studies reveal that the costs for their treatment comprise more than 10% of the people's income per capita.

When considering the magnitude and global impact of theses diseases, especially tooth decays and gingivitis, it is very discouraging that more efficient therapeutic ways and forms to control and eradication of these diseases have not yet been found.

PREVIOUS ART

The odontological science has mainly focused on correcting, restoring, rehabilitating the damage caused. With regard to prevention, actions aimed to improve tooth resistance against bacterial attack through the consumption of fluoridated water or through topic application at the dentist office have been implemented. Additionally, a controlled carbohydrate intake within diet, and daily removing of bacterial plaque by means of mouthwashes containing chlorhexidine gluconate, cetylpirydinium chloride, thymol among other. Even though the impact of these approaches is evident, the optimal control levels in subjects have not been achieved and there still remain high risk groups.

Nowadays, more modern efforts have been focused on the search of safer antimicrobial drugs aimed at treating the causes of oral pathologies and not their effects, attaching this type of therapy a greater importance.

By reviewing the existing pharmaceutical products within the odontological scope, a number of products can be mentioned in the form of mouthwash, gels, toothpaste, etc., which incorporate several active agents. Among the best known products are Listerine®, a widely used oral mouthwash containing thymol and other essential oils as menthol and eucalyptus as active substances. Other mouthwashes use triclosan or cetylpirydinium chloride as active substances and large amounts of alcohol, between 25 and 30% v/v. Alcohol is used as a vehicle and as a solvent for active substances and as excipients for solution homogenization. However, the large amount of alcohol contained in mouthwashes has been widely questioned.

The vast majority of dental product contains fluorides whose function is to strengthen dental enamel against the acid attack of bacteria, describing likewise an antibacterial property.

Other pastes, gels or mouthwashes include chlorhexidine gluconate, a substance of antibacterial action used in the treatment of periodontal diseases.

Briefly, oral hygiene products and more specifically, mouthwashes can be classified into 2 types, cosmetic ones, designed to refresh breath and inhibit bad taste without having a specific function on germs, and pharmaceutical products which help control pathogenic oral microorganism by including antibacterial active substances as phenol, chlorophenol derivatives as chlorhexidine and antiplaque agents as sodium benzoate.

Among related patents, U.S. Pat. No. 6,348,187 by Pan et at, describe a formulation in the form of mouthwash useful for preventing or reducing bad breath, bacterial plaque and gum diseases comprising a combination of thymol and one or more active essential oils, optionally comprising ethanol in an amount above 30% v/v; between 0.1 and 8% of hydrogen peroxide w/v; at least one surfactant in an enough amount to solubilize the essential oils and water. This formulation is provided in 2 separate solutions, which should be mixed before using.

U.S. Pat. No. 5,104,644 describes a formulation in the form of a mouth wash containing between 0.5 and 3% w/v of hydrogen peroxide, at least 0.02% w/v of zinc chloride, at least 0.04% w/v of sodium lauryl sulfate, at least 0.08% w/v of sodium citrate and between 2 a 3.5% p/v of ethanol. Mint oil and menthol are used as flavor agents. This patent claims the ability to destroy bacteria preventing dental diseases.

European patent No 0 161 899 by Saxton et al, describes a non cationic antibacterial and antiplaque agent containing hydroxidiphenil ether, triclosan in combination with zinc citrate.

Chilean patent No. 44471 describes a formulation in the form of a mouthwash and other forms useful for treating periodontal diseases and halitosis which consists of a mixture between 0.01 to 0.5% 0.01 a 0.5% w/w of hydrogen peroxide, between 0.001 and 0.5% w/w of eugenol, 0.001 to 0.5% w/w of parachlorophenol, 0.001 to 0.3% w/w of camphor among other ingredients. This formulation contains no ethanol and claims the treatment of periodontal diseases as well as the avoidance of plaque formation, cavity development reduction, and tartar developing inhibition.

Within the scope of odontological therapeutics and preventive odontology, it would be then more desirable, a formulation that could demonstrate effectiveness in the treatment of microbial oral diseases, be effective in preventing such diseases, control the halitosis, produce a high degree of oral hygiene without altering the oral microbiotic balance, and without restricting the use through dental staining, taste alteration or oral mucosa irritation.

DISCLOSURE OF THE INVENTION

In previous art, inventions have been found to mainly describe a mixture of active substances derived from essential oils together with phenolic compounds and oxidants. Studies conducted demonstrate certain concerns with regard to biocompatibility, even in reduced concentrations, of compounds derived from phenols or chlorophenols, an example of which are the organoleptic-type restrictions for parachlorophenol imposed by the US Environmental Protection Agency EPA) which restricts the contents of this compound to no more than 0.1 ug/l in water for human consumption. However, technical limitations derived from the use of "organoleptic" criteria upon defining quality parameters are recognized.

On the other hand, in USA, products for oral hygiene containing chlorhexidine gluconate, one of the main compounds used for the treatment of serious gingival diseases due to its bactericidal character, are regulated and thus their commercialization is not allowed over the counter, and their use is limited and only with medical prescription since in some patients permanent coloration on some teeth or other oral areas, taste changes as well as different degrees of oral irritation may occur.

In order to create an over the counter product, without use limitations such as chlorhexidine, wherein chlorphenolic compounds will be replaced and to carry out a type of specific antibacterial medical therapy against gems such as *Streptococcus mutans* and *lactobacillus*, major cause of tooth decay; porphyromonas gingivalis, which causes different degrees of gingivitis and *Solobacterium moorei* which produces halitosis, this broad spectrum polyantiseptic composition is provided which mainly consists of a mixtures of 2 essential oils in the presence of oxidative agents and other actives intended to fight against these diseases.

This formulation in the form of mouthwash, gel, toothpaste or other forms of use, without alcohol, comprises the following components:

1. Hydrogen peroxide, present within a range of between 0.05 and 0.3% w/w, preferably between 0.05 and 0.2% w/w, and more preferably between 0.05 and 0.1% w/w. This compound, a weak acid of bactericidal effect which inhibits the development of *Streptococcus mutans*, is a chemical inhibitor of the bacterial plaque and specifically acts on anaerobic microorganism due its ability to generate oxygen free radicals. In the present invention, hydrogen peroxide is preferably used in aqueous solution directly added to the composition, being also possible the addition thereof in the form of carbamide peroxide, a combination of hydrogen peroxide-urea, which is water soluble, containing around 36% w/w of active hydrogen peroxide which is released upon contacting enzyme catalasa found in saliva.

2. Eugenol, an essential oil which is present within a range of between 0.001 and 0.03% w/w, preferably, between 0.001 and 0.02% w/w and more preferably between 0.005 and 0.01% w/w.

This component is an antiseptic and a disinfectant which also exerts an anti-inflammatory and analgesic effect.

3. Camphor, an aromatic, terpenoid compound comprised in the camphor tree essential oil and present in the formulation within the ranges of between 0.001 and 0.01% w/w and preferably, between 0.001 and 0.007% w/w. It possesses anti-inflammatory and antiseptic properties and acts as a mild local anesthetic agent providing a cooling feeling similar to that of menthol.

4. Zinc salts or other components derived form Zinc or else derived form heavy metals such as silver, mercury, copper, tin, or mixtures thereof, used within a wide range of products related to human health care have been known to have antiseptic properties. Zinc, a natural mineral, widely used in products for human consumption recognized as GRAS which stands for "(Generally Recognized as Safe") by the FDA, is very important for the growth, development and health of the human body, in this formulation it is present within the range between 0.001 and 0.5% w/w and, preferably, between 0.005 and 0.2% w/w and more preferably, between 0.009 and 0.1% w/w. It possesses antiviral ability and it has been used for the treatment of herpes simplex, improves the healing of wounds mainly caused by bums or surgical incisions, reduces and prevents the development of bacterial plaque and the neoformation of supragingival dental tartar. Preliminary studies demonstrates a reducing effect on halitosis and a certain degree of action on oral aphthous ulcers and recurrent aphthous stomatitis, mucositis and candidiasis especially in immunosuppressed patients o under treatment with radiotherapy. In the present invention, zinc sulfate is preferably used.

5. Fluor, in the form of sodium fluoride, sodium monofluorophosphate or other salts which release fluor, has the ability to be incorporated into the dental enamel when it is consumed, making teeth stronger against decay. It is incorporated into the formulation within ranges of between 1 to 1.2% w/w. Sodium fluoride in aqueous solutions or in pastes or dental gels, visibly reduces the frequency or incidence of tooth decay in children and adults, exerting also a dentin desensitizing action. An antibacterial action is attributed to zinc due to the oxidant nature thereof on bacteria.

6. Xylitol, a sweet pentane-penthol, which is a natural constituent of many fruits and vegetables, widely used as a sweetener for sugar free products, pharmaceutical products and for oral hygiene. An anticancer capacity is attributed to xylitol since it is not fermentable by cariogenic bacteria and it is cariostatic because stops the development of decays and inhibits the proliferation of *Streptococcus mutans* avoiding the development of new carious lesions. It is incorporated to the formulation within a range of between 2 to 7% w/w.

7. Cetylpyridinium chloride is a quaternary ammonium compound, non toxic on the skin and mucosal membranes; the antiseptic action thereof is based on the interaction of the cetylpyridinium alkaline ions over bacteria acid molecules thus inhibiting their normal metabolism. Even though it is considered a first generation antiseptic (low substantivity) and very low power, added in amounts between 0.002 to 0.05% w/w to the formulation, synergically enhances the antiseptic action, potentiates the bactericidal effect on microorganisms present in the dorso lingual area and prevents the formation of tongue coating for best results in vivo.

8. Excipients, which consist of authorized colorant and flavor agents, sweeteners, demineralized water among others, based on their form of presentation (gel, paste, mouth wash among others), in an enough amount to complete 100% of the composition.

Depending on the format of presentation, that is to say, different forms of active release matrices, the formulation method is relatively simply which basically consists of preparing a homogeneous solution containing the active components at the defined ratios. Then, preparing the homogeneous solution of each non active component such as flavor, colorant agents and excipients to immediately mix both previous solutions and add the enough amount of water to homogeneity. Finally, the mix prepared with the active release vehicle should be added according to the presentation format.

To counteract possible reduction of antibacterial activity by eliminating relevant anti-plaque non cationic compounds such as chlorophenol, such compound will be replaced by a zinc salt, cationic compound that has highly effective characteristics against oral bacteria and against tooth bacterial plaque formation and that could enhance effectiveness. It is widely known that the combination of cationic compounds such as zinc and other metals, together with non cationic antibacterial compounds such as eugenol, produces a very desirable effect against the formation of plaque thus avoiding gingivitis or tooth decay.

In effectiveness trails in vitro on a mouthwash prepared with the compounds described herein against *S. mutans*, a highly effectiveness against de development of bacterial colonies could be observed.

The trial consisted of two series of agar plates Muller Hinton, with strains of *S. mutans* ATCC 35668, which were cultivated in microaereofilia over 48 hours. In the first series of plates containing the mouthwash with the formulation studied, no development of bacteria was observed. The agar MH control plates, without mouthwash showed a high development of *S. mutans* ATCC 35668.

EXAMPLES

Examples of the pharmaceutical composition preparation are described as follows.

Example 1

Mouthwash

| Component | Amount (parts) |
|---|---|
| Hydrogen peroxide | 0.200 |
| eugenol | 0.100 |
| camphor | 0.050 |
| xylitol | 3.000 |
| zinc sulfate | 0.050 |
| CPC | 0.05 |
| sodium fluoride | 0.0001 |
| excipients csp | 100 |

These ingredients are mixed in demineralized water under continuous shaking until reaching a thoroughly homogeneous solution.

| Component | Amount (parts) |
|---|---|
| carbamide peroxide | 0.200 |
| eugenol | 0.100 |
| camphor | 0.050 |
| xylitol | 3.000 |
| zinc sulfate | 0.050 |
| Sodium fluoride | 0.0001 |
| CPC | 0.002 |
| glycerol | 25.00 |
| xanthan gum | 0.260 |
| sodium saccharin | 0.170 |
| titanium dioxide | 1.000 |
| water | 3.00 |
| sodium hydroxide (40%) | 0.280 |
| sodium lauryl sulfate | 1.760 |
| excipients csp | 100 |

The ingredients are mixed to homogeneity, to form a white toothpaste and it is introduced into aluminum or plastic tubes.

Example 3

Gel-Type Toothpaste

| Component | Amount (parts) |
|---|---|
| carbamide peroxide | 0.200 |
| eugenol | 0.100 |
| camphor | 0.050 |
| xylitol | 3.000 |
| zinc sulfate | 0.050 |
| Sodium fluoride | 0.0001 |
| CPC | 0.002 |
| glycerol | 25.00 |
| xanthan gum | 0.260 |
| sodium saccharin | 0.170 |
| titanium dioxide | 1.000 |
| water | 3.00 |
| syloblanc 81C | 20.00 |
| sodium lauryl sulfate | 1.760 |
| excipients csp | 100 |

These ingredients foil clear gel type toothpaste which is introduced into aluminum or plastic tubes.

The invention claimed is:

1. An antiseptic pharmaceutical composition useful for oral hygiene and for the treatment of oral diseases of microbial origin, comprising, by weight of the composition, 0.1% hydrogen peroxide or the equivalence thereof in carbamide peroxide, 0.01% eugenol, 0.001% to 0.007% camphor, 0.001% to 0.5% metal salt selected from the group consisting of a zinc salt, a sliver salt, a copper salt, and a tin salt, a mixture thereof, 1% sodium fluoride; 2% to 7% xylitol, 0.002% cetylpyridinium chloride, and and excipient.

2. The pharmaceutical composition according to claim 1, wherein the zinc salt comprises 0.005% to 0.2% zinc sulfate.

3. The pharmaceutical composition according to claim 1, comprising 0.009% to 0.1% zinc sulfate.

4. The pharmaceutical composition according to claim 1, comprising 0.005% camphor, 0.01% zinc sulfate, and 5% xylitol.

5. The pharmaceutical composition according to claim 1, wherein the metal salt is a zinc compound selected from the group consisting of a lactate, a carbonate, a citrate, an oxide, a borate, a benzoate, and a salicylate.

6. The pharmaceutical composition according to claim 1, wherein the metal salt is selected from the group consisting of a salt of silver, mercury, copper, and tin.

7. The pharmaceutical composition according to claim 1, in the form that includes a mouthwash, a gel, and a toothpaste.

8. Method of formulating a pharmaceutical composition according to claim 1, consisting essentially of:
   a. preparing an homogeneous solution containing active components at defined ratios;
   b. preparing an homogeneous solution of each non active components such as flavor, color agents and excipients;
   c. mixing both previous solutions and adding an enough amount of water to homogeneity; and
   d. adding the prepared mixture to the active release vehicle according to the format presentation.

9. A method for treating the oral cavity, comprising the steps of:
   a) providing a medicament that comprises a pharmaceutical composition, according to claim 1, and
   b) applying the medicament to the oral cavity.

10. The method according to claim 9, wherein the applying ste provides one or more of:
   a) deodorizing, astringing and soothing inflammation of the oral area, avoiding the formation and neoformation of tartar;
   b) treating an oral disease including periodontal diseases, cavities, halitosis, mucositis, mycosis, oral aphthous ulcers, herpes and candidiasis;
   c) irrigating and curing odontological lesions including periodontal bags, fistulae, abscesses, alveolitis, necrosis and pulp gangrene;
   d) preventing or avoiding oral diseases during orthodontic treatments, oral surgeries, and patients wearing fixed and detachable prostheses;
   e) relieving, reducing, curing or preventing oral diseases in patients undergoing radiotherapy or chemotherapy, in hospitalized patients, and in terminally ill patients; and
   f) relieving, reducing, curing or preventing oral diseases in patients suffering from nutritional, endocrine, hematological, cardiovascular and psychosomatic disorders, including patients who are physically or mentally weakened and patients with genetic or hereditary alterations.

11. The antiseptic pharmaceutical composition according to claim 1 wherein the composition is useful for the treatment of oral diseases caused by *Streptococcus mutans, porphyromonas gingivalis, Solobacterium moorei* and/or *lactobacillus*.

12. The method for treating oral diseases caused by *Streptococcus mutans, porphyromonas gingivalis, Solobacterium moorei* and/or *lactobacillus*, comprising the steps of:
   a) providing the composition of claim 1; and
   b) applying the composition to the oral cavity to treat an oral disease caused by *Streptococcus mutans, porphyromonas gingivalis, Solobacterium moorei* and/or *lactobacillus*.

* * * * *

UNITED STATES PATENT AND TRADEMARK OFFICE
CERTIFICATE OF CORRECTION

| | |
|---|---|
| PATENT NO. | : 8,865,136 B2 |
| APPLICATION NO. | : 13/391334 |
| DATED | : October 21, 2014 |
| INVENTOR(S) | : Tomás Bernardo Galván González |

It is certified that error appears in the above-identified patent and that said Letters Patent is hereby corrected as shown below:

In the Specification

Column 3, line 58, delete "bums" and insert --burns--

Column 6, line 1, delete "foil" and insert --form--

In the Claims

Column 6, Claim 1, lines 7-8, delete "of a zinc salt, a sliver salt, a copper salt, and a tin salt, a mixture thereof," and insert --of a zinc salt, a silver salt, a mercury salt, a copper salt, and a tin salt, and a mixture thereof,--

Column 6, Claim 1, line 9, delete "and and" and insert --and--

Column 6, Claim 10, line 2, delete "ste" and insert --step--

Signed and Sealed this
Twenty-second Day of September, 2015

Michelle K. Lee
*Director of the United States Patent and Trademark Office*